(12) United States Patent
Mao et al.

(10) Patent No.: US 10,073,109 B2
(45) Date of Patent: Sep. 11, 2018

(54) PHAGES OF BIOMARKER CAPTURE AND METHODS OF USE

(71) Applicant: The Board of Regents of the University of Oklahoma, Norman, OK (US)

(72) Inventors: Chuanbin Mao, Norman, OK (US); Binrui Cao, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/565,105

(22) PCT Filed: Apr. 5, 2016

(86) PCT No.: PCT/US2016/026031
§ 371 (c)(1),
(2) Date: Oct. 6, 2017

(87) PCT Pub. No.: WO2016/164357
PCT Pub. Date: Oct. 13, 2016

(65) Prior Publication Data
US 2018/0203026 A1 Jul. 19, 2018

Related U.S. Application Data

(60) Provisional application No. 62/143,450, filed on Apr. 6, 2015.

(51) Int. Cl.
*G01N 33/68* (2006.01)
*G01N 35/00* (2006.01)
*G01N 33/569* (2006.01)
*G01N 33/543* (2006.01)
*C07K 7/08* (2006.01)
*A61K 38/04* (2006.01)

(52) U.S. Cl.
CPC ........... *G01N 35/0098* (2013.01); *C07K 7/08* (2013.01); *G01N 33/54326* (2013.01); *G01N 33/56983* (2013.01); *A61K 38/04* (2013.01)

(58) Field of Classification Search
None
See application file for complete search history.

(56) References Cited

U.S. PATENT DOCUMENTS

2012/0045828 A1    2/2012   Davis et al.
2013/0295585 A1   11/2013   Stayton et al.

OTHER PUBLICATIONS

Massart, R.; "Preparation of Aqueous Magnetic Liquids in Alkaline and Acidic Media"; IEEE Transactions on Magnetics, vol. Mag-17, No. 2; Mar. 1981; 1247-1248.

(Continued)

*Primary Examiner* — Changhwa J Cheu
(74) *Attorney, Agent, or Firm* — Hall Estill Law Firm

(57) ABSTRACT

Disclosed are genetically-modified phages, comprising a first nucleic acid sequence encoding at least a first peptide able to bind to a magnetic nanoparticle, and a second nucleic acid sequence encoding at least a second peptide able to bind with high specificity to a predetermined biomarker, and a method for using the genetically-modified phage displaying the first peptide and second peptide in a method for analyzing a fluid sample for the predetermined biomarker.

15 Claims, 5 Drawing Sheets

Specification includes a Sequence Listing.

(56) References Cited

OTHER PUBLICATIONS

Petrenko, V.A., et al.; "A library of organic landscapes on filamentous phage"; Protein Engineering; vol. 9, No. 9; 1996; 797-801.

Ghadjari, A., et al.; "Epitope mapping Candida albicans proteinase (SAP 2)"; FEMS Immunology and Medical Microbiology; vol. 19; 1997; 115-123.

Smith, G.P., et al.; "Phage Display"; Chem, Rev.; vol. 97; 1997; 391-410.

Chen, X., et al.; "Protection of rhesus macaques against disease progression from pathogenic SHIC-89.6PD by vaccination with phage-displayed HIV-1 epitopes"; Nature Medicine; vol. 7, No. 11; Nov. 2001; 1225-1231.

Morrison, C.J., et al.; "Competitive Binding Inhibition Enzyme-Linked Immunosorbent Assay That Uses the Secreted Aspartyl Proteinase of Candida albicans as an Antigenic Marker for Diagnosis of Disseminated Candidiasis"; Clinical and Diagnostic Laboratory Immunology; vol. 10, No. 5; Sep. 2003; 835-848.

Yang, Q., et al.; "Production of hybrid phage displaying secreted aspartyl proteinase epitope of Candida albicans and its application for the diagnosis of disseminated candidiasis"; Journal Compilation, Blackwell Publishing Ltd, Mycoses, vol. 50; 2007; 165-171.

Cao, B., et al.; "Identification of Microtubule-Binding Domains on Microtubule-Associated Proteins by Major Coat Phage Display Technique"; Biomacromolecules; vol. 10; 2009; 555-564; (published on Web Feb. 2, 2009).

Wittenberg, N.J., et al.; "Using nanoparticles to push the limits of detection"; WIREs Nanomed Nanobiotechnol; vol. 1; Mar./Apr. 2009; 237-254.

Liu, A., et al.; "Nanocomposite Films Assembled from Genetically Engineered Filamentous Viruses and Gold Nanoparticles: Nanoarchitecture- and Humidity-Tunable Surface Plasmon Resonance Spectra"; Advanced Materials; vol. 21; 2009; 1001-1005.

Mao, C., et al.; "Virus-Based Chemical and Biological Sensing"; Angew. Chem. Int. Ed.; vol. 48; 2009; 6790-6810.

Perera, K., et al.; "Development of an indirect ELISA for the detection of serum IgG antibodies against region IV of phase 1 flagellin of *Salmonella enterica* serovar Brandenburg in sheep"; Journal of Medical Microbiology; vol. 58; 2009; 1576-1581.

Abbineni, G., et al.; "Evolutionary Selection of New Breast Cancer Cell-Targeting Peptides and Phages with the Cell-Targeting Peptides Fully Displayed on the Major Coat and Their Effects on Actin Dynamics during Cell Internalization"; Molecular Pharmaceutics; vol. 7, No. 5; 2010; 1629-1642; (published on Web Jul. 26, 2010).

Seker, U.O.S., et al.; "Material Binding Peptides for Nanotechnology"; Molecules; vol. 16; Feb. 9, 2011; 1426-1451.

Ghosh, D., et al.; "M13-templated magnetic nanoparticles for targeted in vivo imaging of prostate cancer"; Nature Nanotechnology; vol. 7; Oct. 2012; 677-682.

Lerner, M.B., et al.; "Hybrids of a Genetically Engineered Antibody and a Carbon Nanotube Transistor for Detection of Prostate Cancer Biomarkers"; ACS Nano; vol. 6, No. 6; 2012; (published online May 10, 2012); 5143-5149.

Lee, J.H.; "Amplified Protein Detection and Identification through DNA-Conjugated M13 Bacteriophage"; ACS Nano; vol. 6, No. 6; 2012; (published online May 15, 2012); 5621-5626.

Ma, K.; et al.; "Synergetic Targeted Delivery of Sleeping-Beauty Transposon System to Mesenchymal Stem Using LPD Nanoparticles Modified with a Phage-Displayed Targeting Peptide"; Adv. Funct. Mater.; vol. 23; 2013; 1172-1181.

Nikazar, M., et al.; "The optimum conditions for synthesis of Fe3O4/ZnO core/shell magnetic nanoparticles for phodegradation of phenol"; Iranian Journal of Environ. Health Sci. & Eng.; vol. 12, No. 21; 2014; 1-6.

Yuan, L., et al.; "Ultrasensitive IgG quantification using DNA nano-pyramids"; NPG Asia Materials; vol. 6; 2014; 1-8.

Wang, Y., et al.; "Ultrasensitive Rapid Detection of Human Serum Antibody Biomarkers by Biomarker-Capturing Viral Nanofibers"; ACS Nano; vol. 9, No. 4; 2015 (published online Apr. 9, 2015); 4475-4483.

PCT/US2016/026031; International Search Report and Written Opinion; dated Aug. 19, 2016; 14 pages.

PHAGES OF BIOMARKER CAPTURE AND METHODS OF USE

CROSS-REFERENCE TO RELATED APPLICATIONS

The present application is a national stage application of a PCT application having International Application No. PCT/US2016/026031, filed Apr. 5, 2016, which claims priority to U.S. Provisional Application having U.S. Ser. No. 62/143,450, filed Apr. 6, 2015, which claims the benefit under 35 U.S.C. 119(e). The disclosure of which is hereby expressly incorporated herein by reference.

BACKGROUND

Sensitive, efficient, and rapid detection of biomarkers is important in patient evaluation and treatment. For example, invasive fungal infection is a major cause of increased mortality in cancer patients or other immunocompromised subjects. 70%-87% of such infections are caused by *Candida* species, especially *Candida albicans* (*C. albicans*) (50%-67%). *C. albicans* can cause bloodstream infection (candidaemia) and/or organ infection (disseminated candidiasis) in immunocompromised individuals such as cancer patients. Both candidaemia and disseminated candidiasis lead to high mortality rates of cancer patients. To reduce such high mortality, it is important to diagnose *C. albicans* infection and initiate antifungal therapy early. However, the blood culture method, the current "gold standard" in the clinical diagnosis of *C. albicans* infection, takes about 5 days to get reliable results, resulting in the delay of antifungal therapies and increased chance of death. On the other hand, other techniques, e.g. enzyme-linked immunosorbent assay (ELISA) for the detection of specific proteins related to *C. albicans* infection, cannot efficiently detect the low levels of marker proteins, such as anti-secreted aspartyl proteinase 2 IgG (anti-Sap2-IgG) which are generated at the early stage of *C. albicans* infection. Therefore, a new strategy with high time-efficiency and sensitivity is needed for the early detection of anti-Sap2-IgG and other such biomarkers. Novel compositions and methods for achieving such results are disclosed hereinbelow.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the inventive concepts disclosed herein. The figures are not necessarily to scale and certain features and certain views of the figures may be shown as exaggerated in scale or in schematic in the interest of clarity and conciseness.

DETAILED DESCRIPTION

Figure 1:
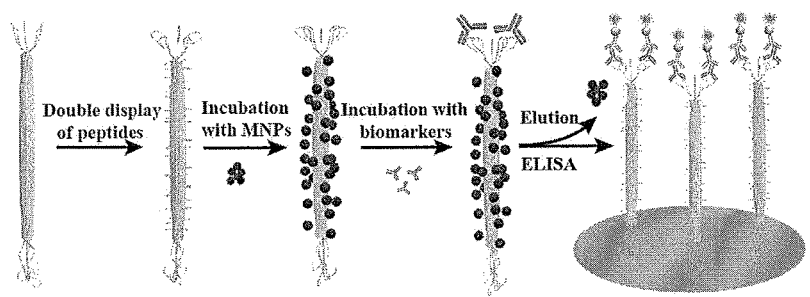
FIG. 1 is a general representation of a novel process using a filamentous phage genetically engineered to display two types of peptides, one for capturing a specific biomarker and another for binding magnetic nanoparticles (MNPs) to form a magnetic virus.

The present disclosure is directed, in at least certain embodiments, to genetically-modified filamentous fd phage structures which display (1) biomarker-specific peptides able to recognize and bind to at least one type of biomarker molecule desired to be detected, and (2) magnetic nanoparticle (MNP)-binding peptides able to bind to MNPs. The genetically-modified phage structure thus displays both types of peptides. The genetically-modified phage structure is exposed to MNPs which bind to the MNP-binding peptides of the phage causing the phage structure to be decorated with MNPs. The MNP-bearing phage structure can then be exposed to a test sample (e.g., serum or other fluid) for detection of the biomarkers specific to the biomarker-specific peptides displayed on the phage structure. The phage-bound biomarker is then magnetically enriched and biochemically detected. This method greatly increases the sensitivity and specificity of the biomarker detection. The average detection time can be completed within several hours, vs conventional culturing methods which often requires about five days for completion. In addition to the reduction in testing time, the detection limit of the methods of the presently disclosed methods is about two orders of magnitude lower than that of the traditional antigen-based methods, opening up new avenues to virus-based disease diagnosis. FIG. 1 is a general representation of a process using a filamentous phage genetically engineered according to the presently disclosed methods to display two types of peptides, one for capturing a specific biomarker and another for binding MNPs to form a magnetic phage virus. The phage virus decorated with the MNPs captures the biomarkers from a fluid sample enabling the captured biomarkers to be magnetically enriched. MNPs are eluted from the enriched sample and the phage particles with the linked biomarker are analyzed with high efficiency, sensitivity and specificity, e.g., by ELISA.

Before further describing various embodiments of the compositions and methods of the present disclosure in more detail by way of exemplary description, examples, and results, it is to be understood that the embodiments of the present disclosure are not limited in application to the details of methods and compositions as set forth in the following description. The embodiments of the compositions and methods of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. All of the compositions and methods of production and application and use thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

The term "mutant" is intended to refer to a protein, peptide, or nucleic acid which has at least one amino acid or nucleotide which is different from the wild type version of the protein, peptide or nucleic acid, and includes, but is not limited to, point substitutions, multiple contiguous or non-contiguous substitutions, chimeras, or fusion proteins, and the nucleic acids which encode them. Examples of conservative amino acid substitutions include, but are not limited to, substitutions made within the same group such as within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, and valine), aromatic amino acids (such as phenylalanine, tryptophan, tyrosine) and small amino acids (such as glycine, alanine, serine, threonine, methionine).

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure. Where used herein the term "high specificity" refers to a specificity of at least 90%, or at least 91%, or at least 92%, or at least 93%, or at least 94%, or at least 95%, or at least 96%, or at least 97%, or at least 98%, or at least 99%. Where used herein the term "high sensitivity" refers to a sensitivity of at least 90%, or at least 91%, or at least 92%, or at least 93%, or at least 94%, or at least 95%, or at least 96%, or at least 97%, or at least 98%, or at least 99%.

The terms "subject" and "patient" are used interchangeably herein and will be understood to refer to a warm blooded animal, particularly a mammal or bird. Non-limiting examples of animals within the scope and meaning of this term include dogs, cats, rats, mice, guinea pigs, horses, goats, cattle, sheep, zoo animals, Old and New World monkeys, non-human primates, and humans.

"Treatment" refers to therapeutic treatments. "Prevention" refers to prophylactic treatment measures to stop a condition from occurring. The term "treating" refers to administering the composition to a patient for therapeutic purposes.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable biochemical and/or therapeutic effect, for example without excessive adverse side effects (such as toxicity, irritation and allergic response) commensurate with a reasonable benefit/risk ratio when used in the manner of the inventive concepts. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "homologous" or "% identity" as used herein means a nucleic acid (or fragment thereof) or a protein (or a fragment thereof) having a degree of homology to the corresponding reference nucleic acid or protein that may be in excess of 70%, or in excess of 80%, or in excess of 85%, or in excess of 86%, or in excess of 87%, or in excess of 88%, or in excess of 89%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877. In at least one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same. Similarly, two amino acid sequences each having 100 residues will have at least 90% identity when at least 90 of the amino acids at corresponding positions are the same.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a protein product (including peptides) including polynucleotides in the form of RNA, such as mRNA, or in the form of DNA, including, for instance, cDNA and genomic DNA obtained by cloning or produced by chemical synthetic techniques or by a combination thereof. Moreover, the peptides of the present disclosure and the nucleic acids which encode them include protein and nucleic acid variants which comprise additional substitutions (conservative or non-conservative). For example, the peptide and nucleic acid variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein, for example the property of binding to a specific biomarker, or to MNPs. Specific examples of such conservative amino acid substitutions include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met. The present disclosure is intended, for example, to include sequences homologous to SEQ ID NOS:1-14 which include one of more of the conservative amino acid substitutions listed hereinabove.

In one non-limiting example, the MNP binding peptide of the phage structure of the present disclosure may be SEQ ID NO:17, represented as $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$; wherein $X_1$=P, $X_2$=T or S, $X_3$=Y, $X_4$=S or T, $X_5$=L, V, or I, $X_6$=L, V, or I, $X_7$=P, $X_8$=R or K, $X_9$=L, V, or I, $X_{10}$=A, $X_{11}$=T or S, $X_{12}$=Q or N, $X_{13}$=P, $X_{14}$=F, and $X_{15}$=K or R. For example, SEQ ID NO:1 is SEQ ID NO:17 where $X_1$=P, $X_2$=T, $X_3$=Y, $X_4$=S, $X_5$=L, $X_6$=V, $X_7$=P, $X_8$=R, $X_9$=L, $X_{10}$=A, $X_{11}$=T, $X_{12}$=Q, $X_{13}$=P, $X_{14}$=F, and $X_{15}$=K.

EXAMPLES

The novel embodiments of the present disclosure, having now been generally described, will be more readily understood by reference to the following examples and embodiments, which are included merely for purposes of illustration of certain aspects and embodiments of the present disclosure, and are not intended to be limiting. The following detailed examples and embodiments are to be construed, as noted above, only as illustrative, and not as limitations of the present disclosure in any way whatsoever. Those skilled in the art will promptly recognize appropriate variations from the various compositions, structures, components, procedures and methods.

Figure 2:
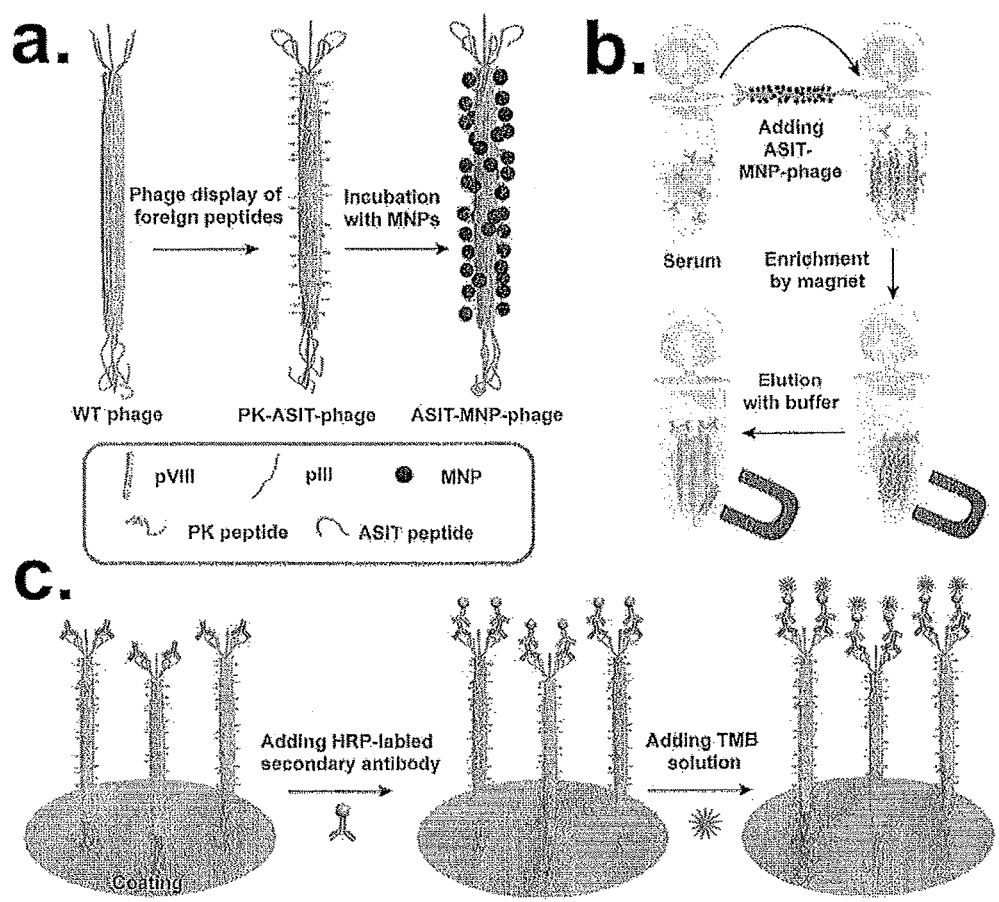
FIG. 2 is a schematic of using ASIT (anti-Sap2-IgG targeting)-MNP-phage for the detection of anti-Sap2-IgG from human serum. (a) Two peptides were double-displayed on the surface of wild type phage (WT phage), with MNP-binding peptide displayed on the pVIII (major coat protein on the phage side wall) and anti-Sap2-IgG-binding peptide displayed on pIII (minor coat protein at the phage tip). MNPs were then bound to the side wall of the resultant phage due to the display of MNP-binding peptides on the major coat, forming ASIT-MNP-phage complex. (b) ASIT-MNP-phage was added to the human sera and captured the biomarker (anti-Sap2-IgG) through its pIII tip. A magnet was then used to enrich the complex of ASIT-MNP-phage and the biomarker. An elution buffer was then used to elute the ASIT-phage/biomarker complex from the MNPs. (c) The eluted ASIT-phage/biomarker complex was coated on the ELISA plate, followed by the addition of horseradish peroxidase (HRP)-labeled secondary antibody that recognized the biomarker. A 3, 3', 5, 5'-tetramethylbenzidine (TMB) coloring solution was further added to the resultant complex to develop color for the detection of the biomarker. PK denotes an MNP-binding peptide having amino acid sequence PTYSLVPRLATQPFK (SEQ ID NO:1). ASIT denotes an anti-Sap2-IgG-targeting peptide having amino acid sequence VKYTS (SEQ ID NO:11). It should be noted that the viral nanofibers are not necessarily vertically oriented on the surface of the plates and the current cartoon is only meant to easily highlight the binding event between viral nanofibers, target antibodies and secondary antibodies.

Phage, as a nontoxic virus, has recently emerged as a new analytical platform. Hence the presently disclosed methods, in at least one embodiment, included use of a novel fd phage functionalized with both anti-Sap2-IgG-targeting (ASIT) peptide (VKYTS-SEQ ID NO:11, an epitope of Sap2, which is able to capture anti-Sap2-IgG[30]) and with peptides able to bind to magnetic nanoparticles (MNPs) to facilitate the capture (by ASIT peptide) and enrichment (by MNPs) of the anti-Sap2-IgG from serum. This was followed by the detection of the biomarker by ELISA (FIG. 2). The fd phage (~900 nm long and 7 nm wide) is a nanofiber-like virus composed of coat proteins surrounding a ssDNA genome that encodes these proteins, including ~3000 copies of a major coat protein (called pVIII) which constitute the side walls and 5 copies each of four minor coat proteins (termed pIII, pVI, pVII, and pIX) which form the two tips. By inserting DNA encoding the desired peptides into the genes of the coat proteins, the peptides are displayed at the tips of the phage by fusion to minor coat proteins and/or along the side walls by fusion to pVIII. This enables the co-display of the two peptides on a single viral nanofiber, including (1) a biomarker-binding peptide, such as but not limited to an ASIT peptide or other peptide sequence (e.g., SEQ ID NO:11-14), at one tip of the phage (as fusion with pIII), which allows the phage to selectively capture the biomarker, e.g., anti-Sap2-IgG, in sera, and (2) an MNP-binding peptide (such as but not limited to SEQ ID NOS: 1-10 and 17) along the side walls (as fusion to pVIII), which enables the decoration of the phage with MNPs for magnetically enriching the captured biomarker, e.g., anti-Sap2-IgG (FIG. 2). The resultant phage (termed herein, for example, as ASIT-MNP-phage) greatly increases the sensitivity for detecting anti-Sap2-IgG (or other biomarker) in sera from cancer patients by ELISA analysis. As noted the biomarker-binding peptide is not limited to the ASIT peptide, but can be any other suitable biomarker-binding peptide which functions in accordance with the present disclosure. Examples of other biomarker-binding peptides which may be used in other embodiments of the present disclosure include, but are not limited to, SQAMDDLMLS (SEQ ID NO:12) for binding to anti-p53 biomarker, CLDGGGKGC (SEQ ID NO:13) for binding to Cysteine-rich intestinal protein 1, and RGD-LATLRQL (SEQ ID NO:14) for binding to αvβ6.

In the genetically-modified phage of the present disclosure, the binding peptides which are displayed on the outer coat of the phage are generally, but not necessarily always, linked to the outer coat at the C-terminal end of the peptide, wherein the N-terminal end of the peptide is free for binding to a magnetic nanoparticle or biomarker protein or peptide.

METHODS

Affinity-Selection of $Fe_3O_4$ MNP-Binding Phage Clones.

We selected the MNP-binding phage clones by following a previously published protocol with minor revision. Specifically, 0.2 mg $Fe_3O_4$ MNPs were re-suspended in 100 μl of binding buffer (100 μl TBS with 0.1% w/w Tween 20). An f88-15mer phage library (~$2\times10^{12}$ phage) was diluted in 1 ml of binding buffer and allowed to interact with a microcentrifuge tube first to remove phages that were bound to the tube materials. The resultant phage library was allowed to interact with MNPs in a microcentrifuge tube for 2 h at 37° C. A magnet was then applied to attract the MNPs along with MNP-bound phage to the bottom of the tube and the supernatant containing non-binding phages was discarded. The MNP-phage pellet was washed five times by repeating the process of resuspension in 1 ml of washing buffer (TBS with 0.1% Tween 20) and the subsequent centrifugation to remove the supernatant. The bound phages were eluted from MNPs with 500 μl of elution buffer (0.1 N HCl, and pH adjusted to 2.2 with glycine) for 7 min on a shaker. The eluate was neutralized by mixing it with 35 μl of 1 M Tris-HCl (pH=9.1) immediately. The entire first-round eluate was amplified by infecting starved E. coli K91 BlueKan cells and the amplified phages were then purified with a double polyethylene glycol (PEG) precipitation method. The purified phages were used as a new input library and the selection procedure as the first round was repeated. After the third round of selection, the eluted phages were not amplified. Instead, the neutralized eluates were titered and 62 colonies were randomly picked up for DNA sequencing.

Construction of a PK-ASIT phage by Phage Double Display Technique.

To insert the DNA sequence which encodes the ASIT binding peptide (VKYTS) into the gene of pIII of phage, an f388-55 RF phage vector was first double digested by BglI (Takara, Japan) and then ligated with the adaptor molecule created by annealing two oligonucleotides (5'-tcgtcaaatatact-tctactg-3'-SEQ ID NO:15; 5'-tagaagtatatttgacgacgt-3'-SEQ ID NO:16) encoding the epitope VKYTS by using T4 DNA ligase (Takara, Japan). The recombinant plasmid (f388-55-VKYTS) was then transformed into competent E. coli MC1061 cells. The positive clones with gene insertion in the phage vector verified by polymerase chain reaction (PCR) were selected for sequencing to confirm the correct insertion of the gene encoding the ASIT binding peptide. The transformed E. coli MC1061 cells were cultured in a shaking incubator at 37° C. overnight to amplify the recombinant plasmid, which was isolated by using a QIAprep Spin Miniprep Kit from Qiagen. To insert the DNA sequence encoding the PK peptide into the gene of pVIII of the phage, the recombinant plasmid was double digested by PstI and HindIII (Takara, Japan) and then ligated with the gene segment encoding the PK peptide. The resultant double-recombinant phage vector (f388-55-ASIT-PK) was transformed into competent E. coli MC1061 cells. The positive clones with gene insertion in the phage vector verified by PCR were further selected for sequencing to confirm the correct insertion of the genes encoding the ASIT and PK peptides. The transformed cells were incubated in a shaking incubator at 37° C. overnight to produce PK-ASIT-phage particles. The phage particles were precipitated and purified by double PEG method.

Serum.

A total of 68 C. albicans-infected cancer patients were enrolled in this study. Those patients were treated at China-Japan Union Hospital of Jilin University, Changchun, Jilin. All patients were given informed consent prior to the collection of their serum samples, and the samples were stored at −80° C. until assayed. The sera from 144 healthy volunteers were kindly provided by Northeast Normal University Affiliated Hospital. Serum samples from a panel of the 144 healthy volunteers were used to determine the cut-off value of the ELISA methods for the detection of the anti-Sap2 antibody. All cases have been analyzed by clinicians.

ELISA Tests for the Detection of Anti-Sap2-IgG Antibody from Serum by ASIT-MNP-phage Method.

800 µl of diluted serum samples were incubated with the ASIT-MNP-phage complexes formed due to the binding interaction between 100 µg MNPs and $4.8 \times 10^{11}$ PK-ASIT-phage particles for 1 h. After incubation, ASIT-MNP-phage complexes, which had captured the anti-Sap2-IgG antibody from serum, were collected and enriched by a magnet and then the MNPs were eluted off ASIT-MNP-phage by using 100 µl of the elution buffer and 15 µl neutralization buffer. MNPs were magnetically removed by a magnet and the phage-bound anti-Sap2-IgG in the remnant solution was coated onto a 96-well plate in 115 µl of carbonate buffer (pH 9.6) for 2 h at 37° C. Next, the plate was blocked with phosphate-buffered saline (PBS) buffer (containing 1% BSA). Then the blocking buffer was discarded. A horseradish peroxidase (HRP)-labeled goat-anti-human IgG (diluted in 1:5000) solution was subsequently added to the wells of the plate and incubated for 45 min. Finally, the unbound HRP-labeled goat-anti-human IgG was removed and 3, 3', 5, 5'-tetramethylbenzidine (TMB) peroxidase substrate solution was added to the plate, followed by incubation for 15 min. The reaction of converting the TMB substrate into a blue product by HRP was stopped by the addition of 2 M $H_2SO_4$, and the absorbance of the resultant yellow product was measured with ELISA reader (Thermo, USA) at 450 nm. All samples were run in triplicate. If the measured $OD_{450nm}$ of one serum sample is higher than the average $OD_{450nm}$ of the 144 serum samples from healthy people plus 3 times of standard deviation,[47] this serum sample was considered as *C. albicans*-infected. The present disclosure is not limited to this threshold for a determination of infection.

Figure 3:
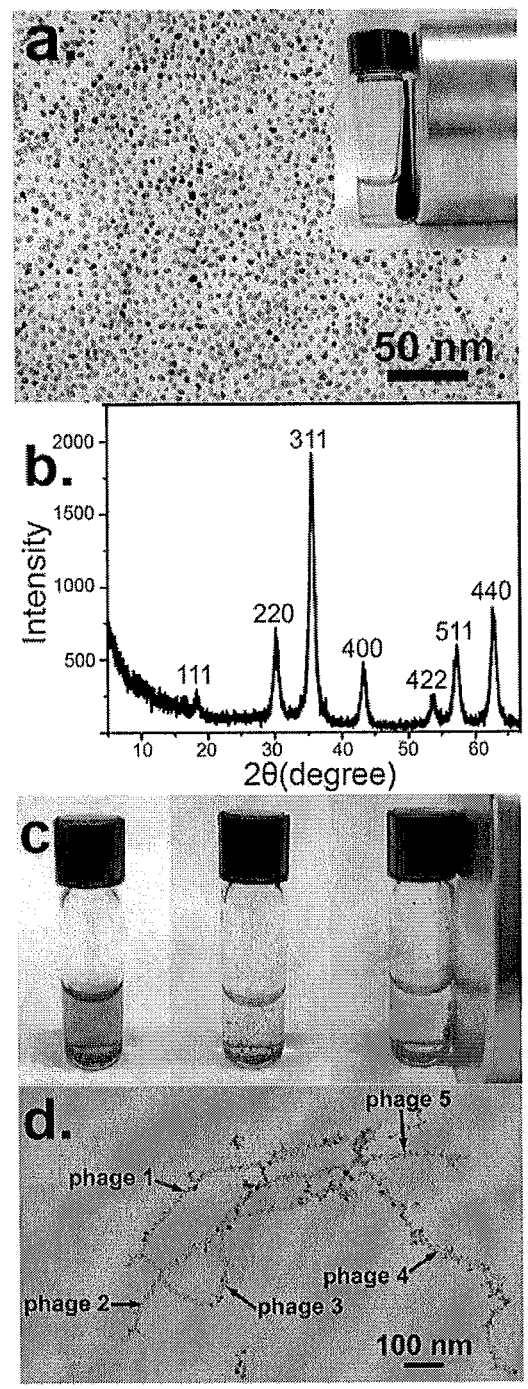
FIG. 3 is a TEM image (a) and XRD pattern (b) of the synthesized MNPs. The inset in (a) shows the attraction of MNPs towards a magnet. (c) Photographs showing MNPs solution (left) and the mixture of MNPs and PK-ASIT-phage (where ASIT-MNP-phage complexes were formed) in the absence (middle) and presence (right) of a magnet. (d) TEM image of the ASIT-MNP-phage complexes shown in (c).
Figure 4:
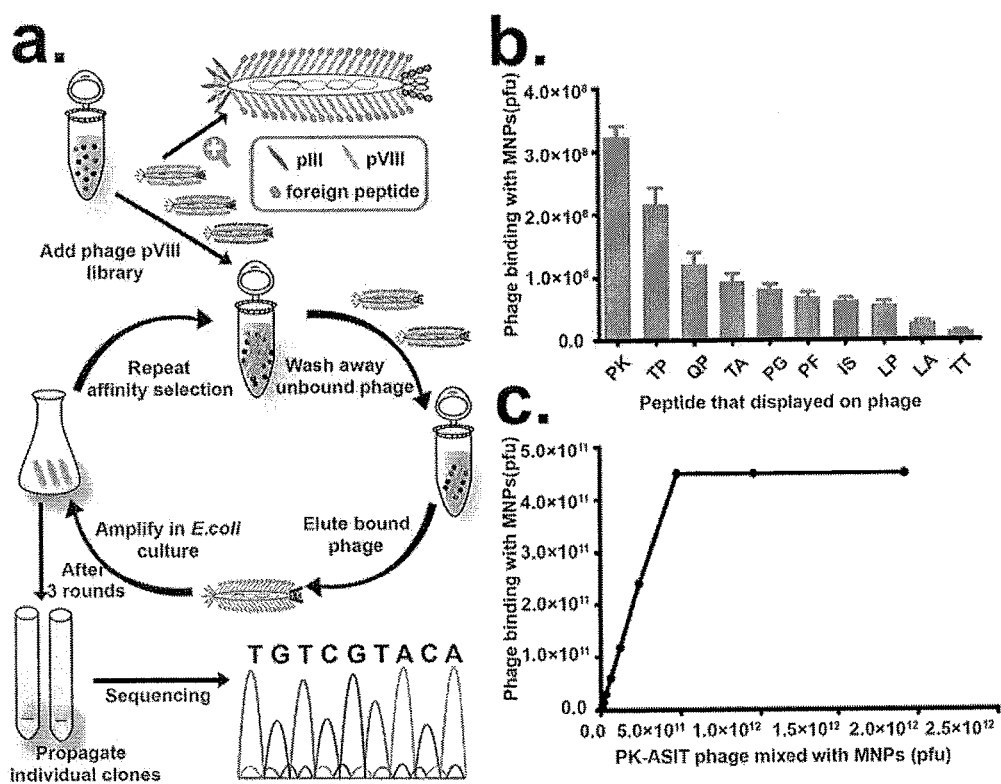
FIG. 4 is a schematic of affinity-selection of MNPs-binding phage (a) and the binding ability of selected phage to MNPs (b and c). (b) Affinity-binding test of selected phages. The amount of phage (input) added to interact with excess MNPs was $3.5 \times 10^8$ pfu and the amount of output (eluted phage) was shown in the plot for phages displaying different peptides (SEQ ID NOS:1-10). The results indicate that the phage displaying PK peptide has the strongest affinity to MNPs. PK=PTYSLVPRLATQPFK (SEQ ID NO:1); TP=TWVASALKNLLYACP (SEQ ID NO:2); QP=QLPSSTPLYATTWQP (SEQ ID NO:3); TA=TVSDEVRLLRLPSTA (SEQ ID NO:4); PG=PSATERLPAQSHPEG (SEQ ID NO:5); PF=PFISYGAQTPLLPVF (SEQ ID NO:6); IS=IRQTRSRTRLSRWAS (SEQ ID NO:7); LP=LRTSPSKQRDHLTSP (SEQ ID NO:8); LA=LALSPQSWPGPANSA (SEQ ID NO:9); TT=TPPSSSLVVLQSKAT (SEQ ID NO:10). (c) Binding tests between MNPs and PK-ASIT-phage. The results show that the maximum amount of PK-ASIT-phage for binding with 100 µg MNPs is $4.5 \times 10^{11}$ pfu.

Water-soluble $Fe_3O_4$ MNPs (~5 nm in diameter), a magnetic label used for enriching specific molecules, were synthesized following a reported protocol and confirmed by transmission electron microscopy (TEM, FIG. 3a), magnetic enrichment (FIG. 3a inset) and X-ray diffraction (XRD, FIG. 3b). MNP-binding peptides were identified from a phage-displayed random peptide library (f88-15mer library, a gift from Dr. George P. Smith at the University of Missouri) by biopanning against the synthesized MNPs following our published protocol (FIG. 4a). We used the pVIII-based phage library instead of the commonly used pIII-based library for two main reasons. First, we want the MNPs to be bound to the side wall of phage (constituted by ~3000 copies of pVIII) by the MNP-binding peptides displayed and the MNP-binding peptides are expected to bind MNPs more efficiently when displayed on the side wall of phage in the same way as when they are selected during biopanning. Second, more candidate peptides are displayed on the side wall than at the tip (made of 5 copies of pIII) of an individual viral nanofiber, leading to more efficient target binding by a phage particle in the pVIII library than in a pIII library during the affinity-selection process.

To start biopanning process, an f88-15mer phage library, which is made of billions of phage clones with each clone displaying a 15-mer peptide on the side wall (pVIII), was allowed to interact with a microcentrifuge tube to remove phages that were bound with the tube. The resultant depleted phage library was used as an input to interact with MNPs placed in a microcentrifuge tube. A magnet was then applied to attract the MNPs along with MNP-binding phages to the bottom of the tube and the supernatant containing non-binding phages was discarded. The MNP-phage pellet was then washed 5 times with washing buffer to get rid of weak MNP-binding phages and the strong MNP-binding phages were eluted using an elution buffer, amplified and used as a new input for the next round of selection. After a binding-washing-elution process was repeated three times, 62 phage clones with high MNP-binding affinity were randomly picked up and sent for DNA sequencing. The sequencing results (see Table S1 of U.S. Provisional Application Ser. No. 62/143,450) show that 2 sequences had 4 repeats, 1 sequence had 3 repeats, 7 sequences had 2 repeats, and 37 sequences only had 1 repeat. Therefore, we picked the 10 sequences with more than 1 repeat (Table S1 of U.S. Provisional Application Ser. No. 62/143,450) for the binding-affinity tests to identify an MNP-binding phage/peptide for further testing. In the binding-affinity tests, 10 phage clones were separately amplified and titered, and the same amount of each phage particle ($3.5 \times 10^8$ pfu) was allowed to interact with excess MNPs. After 5 rounds of washing, the MNP-binding phage particles were eluted, titered and counted. The phage displaying the best MNP-binding peptide should have the highest number of bound phage particles. The results (FIG. 4b) show that the phage displaying the peptide PTYSLVPRLATQPFK (i.e., PK peptide—SEQ ID NO:1) had the highest number of bound phage particles ($3.24 \times 10^8$ pfu), indicating this PK peptide had the highest MNP-binding capability of those tested herein.

The PK peptide, having been selected as the MNP-binding peptide for further testing, and the ASIT-binding peptide (VKYTS-SEQ ID NO:11), were then displayed on the side wall (pVIII) and at the tip (pIII) of phage, respectively (FIG. 2a), forming PK-ASIT-phage. Briefly, the DNA sequences encoding the PK and ASIT peptides were respectively inserted into the specific sites of the genes of pVIII and pIII in the phagemid f388-55. The recombinant f388-55 phagemid was then transformed into *E. coli* MC1061 to produce bio-engineered phage, which displays PK peptide on its side wall (pVIII display) and ASIT peptide at its tip (pIII display) (FIG. 2a). Then, the anti-Sap2-IgG-targeting and MNP-binding abilities of the PK-ASIT-phage were tested. Western blot results (see FIG. S1 of U.S. Provisional Application Ser. No. 62/143,450) show that only PK-ASIT-phage with the pIII displaying ASIT peptide can target anti-Sap2-IgG, while the wild type (WT) phage cannot, confirming the biomarker-binding ability of PK-ASIT-phage. Next, the binding between 100 µg MNPs and different amounts of PK-ASIT-phage was studied (FIG. 4c). The results showed that with the increase of the added phage from $7.5 \times 10^9$ pfu to $1.92 \times 10^{12}$ pfu, the number of bound phage particles increased from $7.2 \times 10^9$ pfu to $4.5 \times 10^{11}$ pfu, indicating PK-ASIT-phage could efficiently bind with MNPs in PBS buffer. But when the added phage was over $4.8 \times 10^{11}$ pfu, the bound phage remained as $~4.5 \times 10^{11}$ pfu, suggesting all the binding peptides displayed on PK-ASIT-phage were occupied by MNPs and confirming $4.5 \times 10^{11}$ pfu is the maximum amount of PK-ASIT-phage for binding with 100 µg MNPs. Therefore, $4.5 \times 10^{11}$ PK-ASIT-phage and 100 µg MNPs were mixed to form ASIT-MNP-phage complexes.

After the mixing of PK-ASIT-phage and MNPs, ASIT-MNP-phage complexes were formed (FIG. 3c-d), in which MNPs were assembled along PK-ASIT-phage. The specificity of the ASIT-MNP-phage complexes was then studied. In the specificity test, ASIT-MNP-phage complexes capturing anti-Sap2-IgG from the sera of cancer patients were collected by a magnet (FIG. 2b) and then the phage-bound anti-Sap2-IgG was eluted off MNPs using an elution buffer for Western blot analysis. It should be noted that the elution buffer was the same as that used to remove MNP-binding phage away from the MNPs during biopanning (FIG. 4a). The Western blot results (FIG. 5a) indicate that anti-Sap2-IgG was specifically captured and detected by ASIT-MNP-phage from the sera of the C. albicans-infected cancer patients (instead of from the sera of the healthy control), confirming the specificity of ASIT-MNP-phage against anti-Sap2-IgG.

Figure 5:
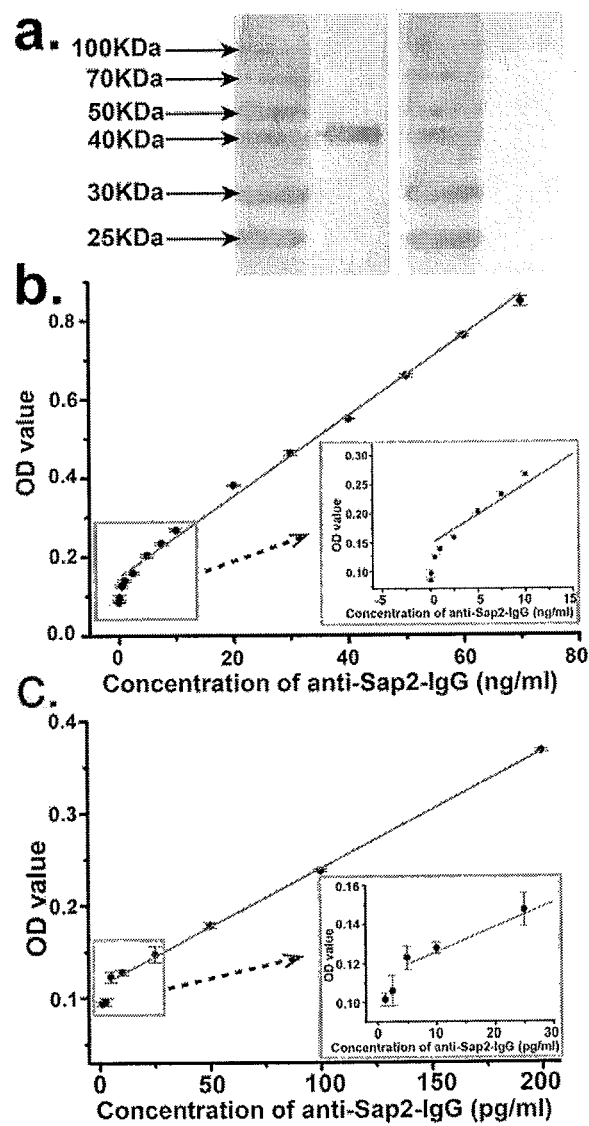
FIG. 5: (a) Western blot analysis showing the specificity of ASIT-MNP-phage for detecting anti-Sap2-IgG in the serum of cancer patients. The data was generated by two steps: First, rSap2 proteins were run on two SDS-PAGE gels and then transferred onto nitrocellulose membranes. Second, the nitrocellulose membranes with Sap2 proteins were divided into two groups, which were incubated with the eluted antibodies collected from serum of patients and healthy control, respectively. Left image: left lane, marker; right lane, serum from *C. albicans*-infected cancer patients. Right image: left lane: marker; right lane, serum from healthy control. (b) Correlation between the ELISA signal (optical density at 450 nm) and the pre-determined concentration of anti-Sap2-IgG in recombinant Sap2 protein-based ELISA method (control). (c) Correlation between the ELISA signal and the pre-determined concentration of anti-Sap2-IgG in ASIT-MNP-phage-based ELISA method.

The high sensitivity of using our ASIT-MNP-phage complexes for detecting anti-Sap2-IgG was confirmed by plotting the pre-designed concentrations of anti-Sap2-IgG, produced and validated through an immunological method (see FIGS. S2 and S3 of U.S. Provisional Application Ser. No. 62/143,450), versus the experimentally determined ELISA signal (FIGS. 5b-c). The detection limit of our ASIT-MNP-phage method was found to be as low as 1.1 pg/ml, two orders of magnitude lower than rSap2-based method (89.56 pg/ml) (see U.S. Provisional Application Ser. No. 62/143,450). In addition, the average detection time for each sample is only about 6 h, much shorter than the clinically used blood culture method which requires about five days.

The ASIT-MNP-phage complexes were then used to detect human anti-Sap2-IgG in sera from patients clinically diagnosed with C. albicans infection by the blood culture method. 68 serum samples from C. albicans-infected cancer patients and 144 serum samples from healthy control were collected and analyzed using the ASIT-MNP-phage-based method described herein. ASIT-phage and rSap2 were used as control detection probes. A cut-off value is defined as the mean plus 3 times standard deviations (SDs) of the absorbance values in the ELISA analysis of these 144 control sera. When the absorbance in ELISA was higher than the cut-off value, the samples were considered infection-positive. By applying this criteria to independent tests, 65±1 out of 68 serum samples from C. albicans-infected cancer patients were detected as infection-positive whereas only 30±2 and 33±2 samples were detected by ASIT-phage and rSap2 methods, respectively (Table 1 and FIG. 4a). These results indicate that the sensitivity of the presently disclosed ASIT-MNP-phage method (95.6% (=65/68×100%)) is much higher than those from the control methods of ASIT phage (44.1% (=30/68×100%)) and rSap2 (48.5% (=33/68×100%)). When ASIT-MNP-phage was applied to detect 144 serum samples from healthy control, only 3 samples were detected as infection-positive (false positive) (Table 1). The detection specificity of ASIT-MNP-phage method reached about 98% ((144−3)/144×100%), a little higher than that of ASIT phage (97.2%) and rSap2 (91.7%) methods. Therefore, the ASIT-MNP-phage method showed a much higher sensitivity and a slightly higher specificity for detecting C. albicans infections within cancer patients than the rSap2 and ASIT-phage methods.

TABLE 1

The number of total C. albicans-infected patients and the average number of cases detected by different assays (Healthy population was used as a control).

| | | Anti-Sap2 positive population | | |
| --- | --- | --- | --- | --- |
| | Population | ASIT-MNP-phage | ASIT-phage | rSap2 |
| Cancer patients with infection | 68 | 65 ± 1 | 30 ± 2 | 33 ± 2 |
| Healthy people | 144 | 3 | 4 ± 1 | 12 ± 1 |

TABLE 2

The number of C. albicans-infected patients with different cancer types and the average number of cases detected by different assays. The ASIT-MNP-phage method identified more candidiasis patients for each cancer type. Systemic C. albicans infection was confirmed by positive blood cultures.

| | | Anti-Sap2 positive population | | |
| --- | --- | --- | --- | --- |
| | Population | ASIT-MNP-phage | ASIT-phage | rSap2 |
| Lung cancer | 21 | 20 ± 1 | 12 ± 1 | 12 ± 1 |
| Breast cancer | 19 | 18 ± 1 | 10 ± 1 | 11 ± 1 |
| Intestinal | 7 | 7 | 3 ± 1 | 4 ± 1 |
| Others | 21 | 20 ± 1 | 5 ± 1 | 6 ± 1 |

Figure 6:
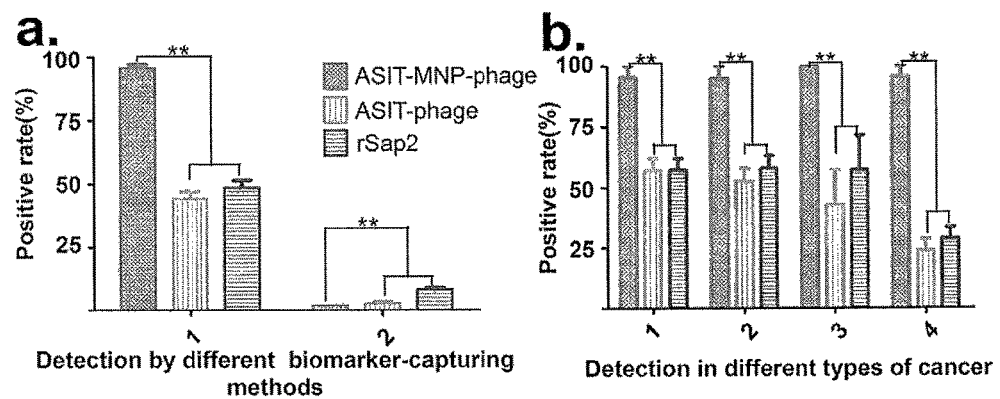
FIG. 6 shows graphs representing the detection of anti-Sap2-IgG in sera of cancer patients with *C. albicans* infection. (a) The percentage of anti-Sap2-IgG positive population among all patients detected using different assays. 1, *C. albicans*-infected patients; 2, Healthy control. Each data point represents the mean for 3 independent experiments ±SD. (b) The percentage of anti-Sap2-IgG positive population among patients of each specific cancer type: 1, lung cancer; 2, breast cancer; 3, intestinal cancer; 4, other cancers. Each data point represents the mean for 3 independent experiments ±SD. **, p<0.01. Both a and b share the same legends as shown in (a).

In addition, we also independently studied the sensitivity of our method in detecting C. albicans infections in patients with different cancer types, including lung cancer (21 samples), breast cancer (19 samples), intestinal cancer (7 samples), and other (21 samples) cancers (Table 2 and FIG. 6b). The ELISA results (FIG. 6b) show that the sensitivity of our ASIT-MNP-phage method was much higher (95.2% (lung cancer), 94.7% (breast cancer), 100.0% (intestinal cancer), and 95.2% (other cancer types) in comparison with ASIT-phage (non-MNP) method (57.1% (lung cancer), 52.6% (breast cancer), 42.9% (intestinal cancer), and 23.8% (other cancer types)) and rSap2 method (57.1% (lung cancer), 57.9% (breast cancer), 47.1% (intestinal cancer), and 28.6% (other cancer types)). These results indicate that ASIT-MNP-phage can be used to detect C. albicans-infected patients having broadly different cancer types.

Description of the production of polyclonal anti-Sap2-IgG in rabbits used for determining detection limit, determination of the limit of detecting anti-Sap2-IgG by using Sap2 protein and the present ASIT-MNP-phage as biomarker-capturing probes in ELISA, the sequencing results of selected phage clones, Western blot for PK-ASIT-phage and wild-type phage with candidiasis serum, ELISA result of the purified anti-Sap2-IgG solutions with a series of dilutions, and Western blotting analysis of anti-Sap2-IgG is shown in U.S. Provisional Application Ser. No. 62/143,450, incorporated by reference herein.

In conclusion, the results of these non-limiting examples show that ASIT-MNP-phage method outperformed ASIT-phage and rSap2 methods in detecting human anti-Sap2-IgG in serum samples. The key to such success lies in the use of magnetic virus (i.e., ASIT-MNP-phage) (FIG. 2). Namely, ASIT-MNP-phage enabled the biomarkers to be magnetically enriched first and then biochemically analyzed. For ASIT phage and rSap2 methods, although both ASIT phage and rSap2 can capture anti-Sap2-IgG with high specificity, they could not enrich the captured anti-Sap2-IgG by means of a magnet. This fact explains why the presently disclosed ASIT-MNP-phage method showed much higher detection sensitivity but a little higher specificity than ASIT phage and rSap2 methods. Furthermore, circulating viruses, which act as antigens, are expected to bind target antibodies more efficiently in solution phase, resulting in more efficient capturing of the antibodies and better detection limit than conventional ELISA method. The high sensitivity of the phage compositions and methods disclosed herein will enhance the early detection of *C. albicans* infection in the cancer patients in intensive care unit. Moreover, as noted above, this virus-based method (e.g., using the MNP-binding peptide, PK peptide) is not limited to the detection of anti-Sap2-IgG using the ASIT peptide having SEQ ID NO:11. Any other binding peptide that can target anti-Sap2-IgG, or other desired biomarker, can be used in the presently-disclosed phage display method, thus the present method can be applied as a general method for detecting biomarkers with high sensitivity and specificity.

In at least certain non-limiting embodiments, the present disclosure is directed to a genetically-modified phage, comprising a first nucleic acid sequence encoding at least a first peptide able to bind to a magnetic nanoparticle, and a second nucleic acid sequence encoding at least a second peptide able to bind with high specificity to a predetermined biomarker protein or peptide. The first peptide may comprise an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17. The second peptide may comprise an amino acid sequence SEQ ID NO:11. The predetermined biomarker protein or peptide may be anti-secreted aspartyl proteinase 2 IgG (anti-Sap2-IgG). The first peptide and the second peptide may be expressed in the genetically-modified phage and displayed on an outer coat thereof. The first peptide may be displayed on a side wall portion of the outer coat and the second peptide may be expressed on a tip portion of the outer coat of the genetically-modified phage. The magnetic nanoparticle may comprise $Fe_3O_4$.

In at least certain non-limiting embodiments, the present disclosure is directed to a phage composition comprising a genetically-modified phage having a first peptide and a second peptide displayed on an outer coat thereof, the first peptide having a magnetic nanoparticle bound thereto, and the second peptide able to specifically bind to a predetermined biomarker protein or peptide. In the phage composition the magnetic nanoparticle bound to the first peptide may comprise $Fe_3O_4$. The first peptide may comprise an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17. The second peptide may comprise an amino acid sequence SEQ ID NO:11. The predetermined biomarker protein or peptide may be anti-secreted aspartyl proteinase 2 IgG (anti-Sap2-IgG).

In at least certain non-limiting embodiments, the present disclosure is directed to a method for detecting a predetermined biomarker protein or peptide in a fluid sample, comprising (1) obtaining a treated genetically-modified phage composition, said treated genetically-modified phage composition formed by combining the fluid sample with a genetically-modified phage having a first peptide and a second peptide displayed on an outer coat thereof, the first peptide having a magnetic nanoparticle bound thereto, and the second peptide able to specifically bind to the predetermined biomarker protein or peptide, (2) enriching the treated genetically-modified phage composition to form a concentrated phage-magnetic nanoparticle composition, (3) removing the magnetic nanoparticles from the concentrated phage-magnetic nanoparticle composition forming a demagnetized phage composition, and (4) analyzing the demagnetized phage composition for the predetermined biomarker protein or peptide. The first peptide of the genetically-modified phage may comprise an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17. The first peptide may be displayed on a side wall portion of the outer coat and the second peptide may be expressed on a tip portion of the outer coat of the genetically-modified phage. The second peptide of the genetically-modified phage may comprise an amino acid sequence SEQ ID NO:11. The predetermined biomarker protein or peptide may be anti-secreted aspartyl proteinase 2 IgG (anti-Sap2-IgG). The method may comprise diagnosing a *Candida* infection in a subject from whom the fluid sample is obtained when the predetermined biomarker protein or peptide is determined to be present in the fluid sample.

It will be understood from the foregoing description that various modifications and changes may be made in the various embodiments of the present disclosure without departing from their true spirit. For example, the processes can be used with any MNP-binding peptide and using any biomarker-specific binding peptide. The description provided herein is intended for purposes of illustration only and is not intended to be construed in a limiting sense. Thus, while certain inventive concepts have been described herein in connection with certain embodiments such as regarding fungal infections so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various components and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

REFERENCES

Yang, Q.; Su, Q. P.; Wang, G. Y.; Wen, D. Z.; Zhang, Y. H.; Bao, H. Z.; Wang, L. Production of Hybrid Phage Displaying Secreted Aspartyl Proteinase Epitope of *Candida Albicans* and Its Application for the Diagnosis of Disseminated Candidiasis. *Mycoses* 2007, 50, 165-171.

Morrison, C. J.; Hurst, S. F.; Reiss, E. Competitive Binding Inhibition Enzyme-Linked Immunosorbent Assay That Uses the Secreted Aspartyl Proteinase of *Candida albi-* cans as an Antigenic Marker for Diagnosis of Disseminated Candidiasis. *Clin. Diagn. Lab. Immun.* 2003, 10, 835-848.

Mao, C.; Liu, A.; Cao, B. Virus-Based Chemical and Biological Sensing. *Angew. Chem. Int. Ed.* 2009, 48, 6790-6810.

Liu, A.; Abbineni, G.; Mao, C. Nanocomposite Films Assembled from Genetically Engineered Filamentous Viruses and Gold Nanoparticles: Nanoarchitecture- and Humidity-Tunable Surface Plasmon Resonance Spectra. *Adv. Mater.* 2009, 21, 1001-1005.

Ghosh, D.; Lee, Y.; Thomas, S.; *Kohli*, A. G.; Yun, D. S.; Belcher, A. M.; Kelly, K. A. M13-Templated Magnetic Nanoparticles for Targeted In Vivo Imaging of Prostate Cancer. *Nat. Nanotechnol.* 2012, 7, 677-682.

Smith, G. P.; Petrenko, V. A. Phage Display. *Chem. Rev.* 1997, 97, 391-410.

Chen, X.; Scala, G.; Quinto, I.; Liu, W.; Chun, T. W.; Justement, J. S.; Cohen, O. J.; vanCott, T. C.; Iwanicki, M.; Lewis, M. G.; et al. Protection of Rhesus Macaques Against Disease Progression From Pathogenic SHIV-89.6PD by Vaccination with Phage-Displayed HIV-1 Epitopes. *Nat. Med.* 2001, 7, 1225-1231.

Petrenko, V. A.; Smith, G. P.; Gong, X.; Quinn, T. A Library of Organic Landscapes on Filamentous Phage. *Protein Eng.* 1996, 9, 797-801.

Lee, J. H.; Domaille, D. W.; Cha, J. N. Amplified Protein Detection and Identification Through DNA-Conjugated M13 Bacteriophage. *ACS Nano* 2012, 6, 5621-5626.

Wittenberg, N. J.; Haynes, C. L. Using Nanoparticles to Push the Limits of Detection. *Wires Nanomed. Nanobio.* 2009, 1, 237-254.

Massart, R. Preparation of Aqueous Magnetic Liquids in Alkaline and Acidic Media. *IEEE Trans. Magn.* 1981, 17, 1247-1248.

Cao, B. R.; Mao, C. B. Identification of Microtubule-Binding Domains on Microtubule-Associated Proteins by Major Coat Phage Display Technique. *Biomacromolecules* 2009, 10, 555-564.

Perera, K.; Murray, A. Development of an Indirect ELISA for the Detection of Serum Igg Antibodies Against Region IV of Phase 1 Flagellin Of *Salmonella Enterica* Serovar Brandenburg in Sheep. *J. Med. Microbiol.* 2009, 58, 1576-1581.

Yuan, L.; Giovanni, M.; Xie, J.; Fan, C.; Leong, D. T. Ultrasensitive IgG Quantification Using DNA Nano-Pyramids. *NPG Asia Mater.* 2014, 6, e112.

Lerner, M. B.; D'Souza, J.; Pazina, T.; Dailey, J.; Goldsmith, B. R.; Robinson, M. K.; Johnson, A. T. C. Hybrids of a Genetically Engineered Antibody and a Carbon Nanotube Transistor for Detection of Prostate Cancer Biomarkers. *ACS Nano* 2012, 6, 5143-5149.

Abbineni, G.; Modali, S.; Safiejko-Mroczka, B.; Petrenko, V. A.; Mao, C. Evolutionary Selection Of New Breast Cancer Cell-Targeting Peptides And Phages With The Cell-Targeting Peptides Fully Displayed On The Major Coat And Their Effects On Actin Dynamics During Cell Internalization. *Mol. Pharm.* 2010, 7, 1629-42.

Ma, K.; Wang, D. D.; Lin, Y.; Wang, J.; Petrenko, V.; Mao, C. Synergetic Targeted Delivery of Sleeping-Beauty Transposon System to Mesenchymal Stem Cells Using LPD Nanoparticles Modified with a Phage-Displayed Targeting Peptide. *Adv. Funct. Mater.* 2013, 23, 1172-1181.

Ghadjari, A.; Matthews, R. C.; Burnie, J. P. Epitope Mapping *Candida Albicans* Proteinase (SAP 2). *Fems Immunol. Med Mic.* 1997, 19, 115-123.

---

What is claimed is:

1. A genetically-modified phage, comprising a first nucleic acid sequence encoding at least a first peptide able to bind to a magnetic nanoparticle, and a second nucleic acid sequence encoding at least a second peptide able to bind with high specificity to a predetermined biomarker protein or peptide, wherein the first peptide comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17.

2. The genetically-modified phage of claim 1, wherein the second peptide comprises an amino acid sequence SEQ ID NO:11, SEQ ID NO:12, SEQ ID NO:13, or SEQ ID NO:14.

3. The genetically-modified phage of claim 1, wherein the predetermined biomarker protein or peptide is anti-secreted aspartyl proteinase 2 IgG (anti-Sap2-IgG).

4. The genetically-modified phage of claim 1, wherein the first peptide and the second peptide are expressed in the genetically-modified phage and are displayed on an outer coat thereof.

5. The genetically-modified phage of claim 4, wherein the first peptide is displayed on a side wall portion of the outer coat and the second peptide is expressed on a tip portion of the outer coat of the genetically-modified phage.

6. The genetically-modified phage of claim 1, wherein the magnetic nanoparticle comprises $Fe_3O_4$.

7. A phage composition comprising a genetically-modified phage having a first peptide and a second peptide displayed on an outer coat thereof, the first peptide having a magnetic nanoparticle bound thereto, and the second peptide able to specifically bind to a predetermined biomarker protein or peptide, wherein the first peptide comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17.

8. The phage composition of claim 7, wherein the magnetic nanoparticle bound to the first peptide comprises $Fe_3O_4$.

9. The phage composition of claim 7, wherein the second peptide comprises an amino acid sequence SEQ ID NO:11, SEQ ID NO:12, SEQ ID NO:13, or SEQ ID NO:14.

10. The phage composition of claim 7, wherein the predetermined biomarker protein or peptide is anti-secreted aspartyl proteinase 2 IgG (anti-Sap2-IgG).

11. A method for detecting a predetermined biomarker protein or peptide in a fluid sample, comprising:
    obtaining a treated genetically-modified phage composition, said treated genetically-modified phage composition formed by combining the fluid sample with a genetically-modified phage having a first peptide and a second peptide displayed on an outer coat thereof, the first peptide having a magnetic nanoparticle bound thereto, and the second peptide able to specifically bind to the predetermined biomarker protein or peptide, wherein the first peptide comprises an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and SEQ ID NO:17;
    enriching the treated genetically-modified phage composition to form a concentrated phage-magnetic nanoparticle composition;
    removing the magnetic nanoparticles from the concentrated phage-magnetic nanoparticle composition forming a demagnetized phage composition; and
    analyzing the demagnetized phage composition for the predetermined biomarker protein or peptide.

12. The method of claim 11, wherein the first peptide is displayed on a side wall portion of the outer coat and the second peptide is expressed on a tip portion of the outer coat of the genetically-modified phage.

13. The method of claim 11, wherein the second peptide of the genetically-modified phage comprises an amino acid sequence SEQ ID NO:11, SEQ ID NO:12, SEQ ID NO:13, or SEQ ID NO:14.

14. The method of claim 11, wherein the predetermined biomarker protein or peptide is anti-secreted aspartyl proteinase 2 IgG (anti-Sap2-IgG).

15. The method of claim 11, comprising diagnosing a *Candida* infection in a subject from whom the fluid sample is obtained when the predetermined biomarker protein or peptide is determined to be present in the fluid sample.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 1

Pro Thr Tyr Ser Leu Val Pro Arg Leu Ala Thr Gln Pro Phe Lys
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 2

Thr Trp Val Ala Ser Ala Leu Lys Asn Leu Leu Tyr Ala Cys Pro
1               5                   10                  15

<210> SEQ ID NO 3
<211> LENGTH: 15
<212> TYPE: PRT
<213> ORGANISM: Artificial Sequence
<220> FEATURE:
```

```
<223> OTHER INFORMATION: Completely synthesized in the lab and of no
      biological origin.

<400> SEQUENCE: 3

Gln Leu Pro Ser Ser Thr Pro Leu Tyr Ala Thr Thr Trp Gln Pro
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 4

Thr Val Ser Asp Glu Val Arg Leu Leu Arg Leu Pro Ser Thr Ala
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 5

Pro Ser Ala Thr Glu Arg Leu Pro Ala Gln Ser His Pro Glu Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 6

Pro Phe Ile Ser Tyr Gly Ala Gln Thr Pro Leu Leu Pro Val Phe
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 7

Ile Arg Gln Thr Arg Ser Arg Thr Arg Leu Ser Arg Trp Ala Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 8

Leu Arg Thr Ser Pro Ser Lys Gln Arg Asp His Leu Thr Ser Pro
1               5                   10                  15
```

```
<210> SEQ ID NO 9
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 9

Leu Ala Leu Ser Pro Gln Ser Trp Pro Gly Pro Ala Asn Ser Ala
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 10

Thr Pro Pro Ser Ser Ser Leu Val Val Leu Gln Ser Lys Ala Thr
1               5                   10                  15

<210> SEQ ID NO 11
<211> LENGTH: 5
<212> TYPE: PRT
<213> ORGANISM: Candida albicans

<400> SEQUENCE: 11

Val Lys Tyr Thr Ser
1               5

<210> SEQ ID NO 12
<211> LENGTH: 10
<212> TYPE: PRT
<213> ORGANISM: Homo sapiens

<400> SEQUENCE: 12

Ser Gln Ala Met Asp Asp Leu Met Leu Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 13

Cys Leu Asp Gly Gly Gly Lys Gly Cys
1               5

<210> SEQ ID NO 14
<211> LENGTH: 10
<212> TYPE: PRT
<213> ORGANISM: Artificial Sequence
<220> FEATURE:
<223> OTHER INFORMATION: Completely synthesized in the lab and of no
      biological origin.

<400> SEQUENCE: 14

Arg Gly Asp Leu Ala Thr Leu Arg Gln Leu
1               5                   10

<210> SEQ ID NO 15
```

```
<211> LENGTH: 21
<212> TYPE: DNA
<213> ORGANISM: Artificial Sequence
<220> FEATURE:
<223> OTHER INFORMATION: Artificially designed and synthesized in the
      lab.

<400> SEQUENCE: 15
tcgtcaaata tacttctact g                                              21

<210> SEQ ID NO 16
<211> LENGTH: 21
<212> TYPE: DNA
<213> ORGANISM: Artificial Sequence
<220> FEATURE:
<223> OTHER INFORMATION: Artificially designed and synthesized in the
      lab.

<400> SEQUENCE: 16
tagaagtata tttgacgacg t                                              21

<210> SEQ ID NO 17
<211> LENGTH: 15
<212> TYPE: PRT
<213> ORGANISM: Artificial Sequence
<220> FEATURE:
<223> OTHER INFORMATION: Completely synthesized in the lab and of no
      biological origin. Consensus sequence.
<220> FEATURE:
<221> NAME/KEY: misc_feature
<222> LOCATION: (2)..(2)
<223> OTHER INFORMATION: Thr or Ser
<220> FEATURE:
<221> NAME/KEY: misc_feature
<222> LOCATION: (4)..(4)
<223> OTHER INFORMATION: Ser or Thr
<220> FEATURE:
<221> NAME/KEY: misc_feature
<222> LOCATION: (5)..(5)
<223> OTHER INFORMATION: Leu, Val, or Ile
<220> FEATURE:
<221> NAME/KEY: misc_feature
<222> LOCATION: (6)..(6)
<223> OTHER INFORMATION: Leu, Val, or Ile
<220> FEATURE:
<221> NAME/KEY: misc_feature
<222> LOCATION: (8)..(8)
<223> OTHER INFORMATION: Arg or Lys
<220> FEATURE:
<221> NAME/KEY: misc_feature
<222> LOCATION: (9)..(9)
<223> OTHER INFORMATION: Leu, Val, or Ile
<220> FEATURE:
<221> NAME/KEY: misc_feature
<222> LOCATION: (11)..(11)
<223> OTHER INFORMATION: Thr or Ser
<220> FEATURE:
<221> NAME/KEY: misc_feature
<222> LOCATION: (12)..(12)
<223> OTHER INFORMATION: Gln or Asn
<220> FEATURE:
<221> NAME/KEY: misc_feature
<222> LOCATION: (15)..(15)
<223> OTHER INFORMATION: Lys or Arg

<400> SEQUENCE: 17

Pro Xaa Tyr Xaa Xaa Xaa Pro Xaa Xaa Ala Xaa Xaa Pro Phe Xaa
1               5                   10                  15
```